United States Patent
Flohr et al.

(10) Patent No.: US 8,619,943 B2
(45) Date of Patent: Dec. 31, 2013

(54) METHOD AND COMPUTER TOMOGRAPHY SYSTEM FOR GENERATING TOMOGRAPHIC IMAGE DATASETS

(75) Inventors: Thomas Flohr, Uehlfeld (DE); Gabriel Haras, Mücke (DE); Daniel Niederlöhner, Erlangen (DE); Stefan Pflaum, Hirschaid (DE)

(73) Assignee: Siemens Aktiengesellschaft, Munich (DE)

( * ) Notice: Subject to any disclaimer, the term of this patent is extended or adjusted under 35 U.S.C. 154(b) by 28 days.

(21) Appl. No.: 13/478,629

(22) Filed: May 23, 2012

(65) Prior Publication Data
US 2012/0300896 A1    Nov. 29, 2012

(30) Foreign Application Priority Data

May 24, 2011 (DE) .......................... 10 2011 076 351

(51) Int. Cl.
*A61B 6/00* (2006.01)
(52) U.S. Cl.
USPC ................................. 378/5; 378/19
(58) Field of Classification Search
USPC ................. 378/4–20; 382/128–132
See application file for complete search history.

(56) References Cited

U.S. PATENT DOCUMENTS

| 7,433,443 | B1 | 10/2008 | Tkaczyk |
| 2007/0205367 | A1 | 9/2007 | Deman |

OTHER PUBLICATIONS

German priority document DE 10 2011 076 351.1 filed May 24, 2011 (not yet published).

*Primary Examiner* — Courtney Thomas
(74) *Attorney, Agent, or Firm* — Harness, Dickey & Pierce, P.L.C.

(57) ABSTRACT

A method and a computed tomography system are disclosed for generating tomographic image datasets of a measurement object with multiple simultaneously operable sets of detector elements. In at least one embodiment, at least one first set measures incident radiation over the entire energy spectrum of the incident radiation in an integrating manner and at least one second set measures incident radiation in at least two energy ranges in a resolving manner, wherein furthermore by way of the integrating measurements, the energy-resolving measurements relating in each case to rays traversing a measurement object in a spatially identical manner are corrected and a tomographic image dataset of the measurement object is reconstructed at least from the corrected energy-resolving measurements.

17 Claims, 2 Drawing Sheets

METHOD AND COMPUTER TOMOGRAPHY SYSTEM FOR GENERATING TOMOGRAPHIC IMAGE DATASETS

PRIORITY STATEMENT

The present application hereby claims priority under 35 U.S.C. §119 to German patent application number DE 10 2011 076 351.1 filed May 24, 2011, the entire contents of which are hereby incorporated herein by reference.

FIELD

At least one embodiment of the invention generally relates to a method and/or a computed tomography system for generating tomographic image datasets of a measurement object with the aid of a computed tomography system (CT system) with at least two simultaneously operable sets of detector elements, which together scan a measurement object from a multiplicity of projection angles, wherein at least one first set of integrating detector elements measures incident radiation over the entire energy spectrum of the incident radiation in an integrating manner and at least one second set of counting detector elements measures incident radiation in at least two energy ranges in a resolving manner.

BACKGROUND

Dual-source CT systems with a conventional integrating scintillation detector and a counting detector are generally known. Here, both measuring systems are simultaneously operated for the scanning of a measurement object, generally a patient. Such a dual-source CT system here contains two emitter-detector systems each comprising one X-ray emitter and the respectively associated detector in each case, which are arranged on a gantry offset at an angle to each other.

One problem of measurements with energy-selective counting detectors consists in the relatively high drift of such detectors as a result of previous irradiation.

SUMMARY

At least one embodiment of the invention is directed to a method and/or a computed tomography system for scanning a measurement object and generating tomographic image datasets from such scanning operations, in the case of which it is not necessary to calibrate the counting detector elements prior to each measurement, in order to compensate for the drift of the detector elements.

The inventors accordingly propose, in at least one embodiment, the improvement of the method for generation of tomographic image datasets of a measurement object with the aid of a computed tomography system (CT system) with at least two simultaneously operable sets of detector elements, which together scan a measurement object from a multiplicity of projection angles, wherein in the known method at least one first set of integrating detector elements measures incident radiation over the entire energy spectrum of incident radiation in an integrating manner, and at least one second set of counting detector elements measures incident radiation in at least two energy ranges in a resolving manner. The inventive improvement here lies in the fact that by way of the integrating measurements of the at least one first set of integrating detector elements, the energy-resolving measurements of the at least one second set of counting detector elements relating in each case to rays passing through a measurement object in a spatially identical manner, are corrected, and at least one tomographic image dataset of the measurement object is reconstructed at least from the corrected energy-resolving measurements of the second set of counting detector elements.

As well as at least one embodiment of the inventive method, a computed tomography system (CT system) in at least one embodiment is also proposed, comprising:

at least two simultaneously operable sets of detector elements for simultaneous scanning of an object under examination from a multiplicity of projection angles, wherein at least one first set of integrating detector elements is designed for integrating radiation measurement and at least one second set of counting detector elements is designed to resolve an incident radiation spectrum into at least two energy bins, and a computer system for the analysis of measurement results from the detector elements with a memory and a computer program located therein, wherein there is also located in the memory of the computer system at least one computer program which during operation carries out the method previously described.

Advantageous developments of the invention are the subject matter of the subordinate claims.

BRIEF DESCRIPTION OF THE DRAWINGS

There follows a more detailed description of embodiments of the invention with the aid of figures, wherein only the features necessary for understanding of the invention are represented. The following reference characters are used: 1: CT system; 2: first X-ray tube; 3: first detector; 4: second X-ray tube; 5: second detector; 6: gantry housing; 7: patient; 8: patient couch; 9: system axis; 10: computer system; 11: contrast agent applicator; 12: ECG line; I: integrating detector element; Prg1-Prgn: computer programs; Z: counting detector element.

Individually, the following are shown.

Figure 1:
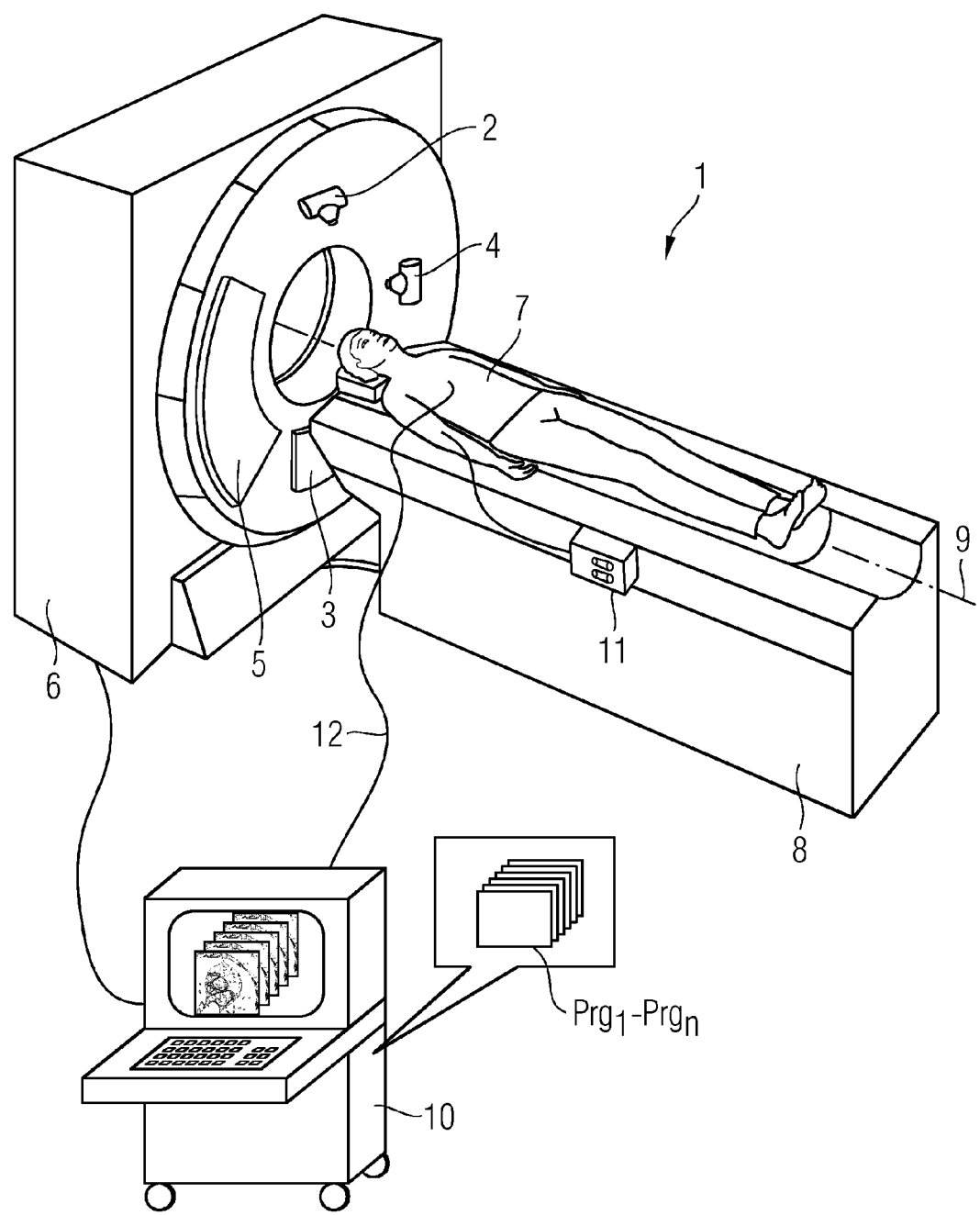
FIG. 1: CT system.

It should be noted that these Figures are intended to illustrate the general characteristics of methods, structure and/or materials utilized in certain example embodiments and to supplement the written description provided below. These drawings are not, however, to scale and may not precisely reflect the precise structural or performance characteristics of any given embodiment, and should not be interpreted as defining or limiting the range of values or properties encompassed by example embodiments. The use of similar or identical reference numbers in the various drawings is intended to indicate the presence of a similar or identical element or feature.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks will be stored in a machine or computer readable medium such as a storage medium or non-transitory computer readable medium. A processor(s) will perform the necessary tasks.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the following description, illustrative embodiments may be described with reference to acts and symbolic representations of operations (e.g., in the form of flowcharts) that may be implemented as program modules or functional processes include routines, programs, objects, components, data structures, etc., that perform particular tasks or implement particular abstract data types and may be implemented using existing hardware at existing network elements. Such existing hardware may include one or more Central Processing Units (CPUs), digital signal processors (DSPs), application-specific-integrated-circuits, field programmable gate arrays (FPGAs) computers or the like.

Note also that the software implemented aspects of the example embodiments may be typically encoded on some form of program storage medium or implemented over some type of transmission medium. The program storage medium (e.g., non-transitory storage medium) may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments not limited by these aspects of any given implementation.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The inventors have recognized the following:

Computed tomography (CT) devices employed in medical applications are today equipped as the prior art with integrating scintillation detectors. In them the incident X-rays are initially converted in a two-stage process into visible light, which is then detected by downstream photodiodes and transformed into electrical signals. Examples of corresponding scintillators are gadolinium oxide or gadolinium oxide sulfide. Such scintillation detectors have a very wide dynamic range and can process the minimum and maximum X-ray flux densities used in medical computed tomography without problems. On the other hand, their spatial resolution is limited, as on mechanical grounds, the detector pixels cannot be reduced in size at will for mechanical and optical separation because of inactive dead zones between the pixels. In addition, integrating scintillation detectors supply no spectral information, so that material characteristic differences in X-ray absorption at different energies of the X-ray spectrum cannot be measured directly. Furthermore, the contrast-to-noise ratio of the detected signals from integrating detectors is not optimum, because the low-energy quanta, which carry the most contrast information, are also only minimally weighted in the integrating detector in accordance with their low energy, so that the contrast of certain materials, such as for instance white and gray brain matter, is thereby reduced.

By contrast, counting detectors exist in which the incoming X-ray quanta are converted into electrical signals and counted in a direct process. Examples of corresponding detector materials are cadmium telluride or cadmium zinc telluride. Counting detectors can be very finely structured on the surface, as the pixels do not have to be mechanically separated and the dead zones thus do not apply. A significantly higher spatial resolution is thus possible than with conventional integrating scintillation detectors. In addition the incident X-ray quanta can be detected for a spectral resolution into different energy bands, as a result of which material characteristic differences in the X-ray absorption at different energies can be registered with a single measurement. Thanks to the possibility of energy-dependent weightings of the contributions to the overall signal it is additionally possible to improve the object contrast and thus the contrast-to-noise ratio in comparison to integrating scintillation detectors.

One disadvantage of counting detectors is, however, the limited dynamic range as a result of the detector materials employed, in the case of which a maximum X-ray flux density must not be exceeded, which according to the current prior art is not sufficiently high for unrestricted use in a medical CT. A further disadvantage is the high drift of the signals from a counting detector after a previous irradiation, wherein under certain circumstances difficult-to-correct artifacts occur in the images.

These problems can however be solved in that parallel measurements of identical or near-identical rays are performed both with integrating detector elements and also with counting detector elements. It is then possible here to compare with each other such measurements of the same rays penetrating the object under examination, and on the one hand to correct the drift of the counting detector elements, preferably on multiple occasions during a scan. Furthermore, measurement data in high dose rate ranges or in the case of photon fluxes which are too high for the counting detector in the saturation range can be augmented with the aid of measurement data from the integrating detectors. This anyway involves measurement data which stems from peripheral areas and regions of the measurement object which are of little diagnostic interest, so that no data valuable for the image reconstruction is also lost.

The inventors accordingly propose, in at least one embodiment, the improvement of the method for generation of tomographic image datasets of a measurement object with the aid of a computed tomography system (CT system) with at least two simultaneously operable sets of detector elements, which together scan a measurement object from a multiplicity of projection angles, wherein in the known method at least one first set of integrating detector elements measures incident radiation over the entire energy spectrum of incident radiation in an integrating manner, and at least one second set of counting detector elements measures incident radiation in at least two energy ranges in a resolving manner. The inventive improvement here lies in the fact that by way of the integrating measurements of the at least one first set of integrating detector elements, the energy-resolving measurements of the at least one second set of counting detector elements relating in each case to rays passing through a measurement object in a spatially identical manner, are corrected, and at least one tomographic image dataset of the measurement object is reconstructed at least from the corrected energy-resolving measurements of the second set of counting detector elements.

In order also to take account of the specific properties of the multiplicity of detector elements employed and their individual differences with reference to a different history of the preceding radiation dosage of the detector elements, it is advantageous if a specific correction factor is formed for each counting detector element.

It is furthermore advantageous if the measurement data from counting detector elements in the saturation range of the counting detector elements is replaced by direct or interpolated measurement data from the integrating detector elements.

As well as at least one embodiment of the inventive method, a computed tomography system (CT system) in at least one embodiment is also proposed, comprising:

at least two simultaneously operable sets of detector elements for simultaneous scanning of an object under examination from a multiplicity of projection angles, wherein at least one first set of integrating detector elements is designed for integrating radiation measurement and at least one second set of counting detector elements is designed to resolve an incident radiation spectrum into at least two energy bins, and a computer system for the analysis of measurement results from the detector elements with a memory and a computer program located therein, wherein there is also located in the memory of the computer system at least one computer program which during operation carries out the method previously described.

In a first advantageous embodiment, in the case of this computed tomography system the at least one first set of integrating detector elements and the at least one second set of counting detector elements are each arranged on physically different detectors.

Alternatively, however, the at least one first set of integrating detector elements and the at least one second set of counting detector elements can also be arranged on one detector, preferably the only one present. The significantly more costly counting detector elements would hereby be at least partially compensated for by saving on the unnecessary second emitter-detector system.

Here the integrating detector elements of the at least one first set and the counting detector elements of the at least one second set can advantageously be arranged grouped into lines or rows to form one detector.

In another embodiment, the integrating detector elements of the at least one first set and the counting detector elements of the at least one second set can also be arranged grouped in a checkerboard fashion to form a detector.

The populated surface of each of the counting detector elements can further be embodied in smaller form than the surface of each of the integrating detector elements. A significantly higher spatial resolution can thus be achieved at least for the counting detector elements.

Shown in FIG. 1 is an example CT system 1 with two emitter-detector systems on a gantry which is not represented in further detail in a gantry housing 6. The two emitter-detector systems, comprising a first X-ray tube 2 with an associated detector 3 lying opposite the first X-ray tube and a second X-ray tube 4 with a detector 5 associated with the second X-ray tube lying opposite this on the other hand, are arranged on the gantry offset at an angle in a rotational plane. According to the invention, the two detectors 3 and 5 can in each case be equipped with detector elements which differ in their function, so that one detector is equipped with counting detector elements, and the other detector with integrating detector elements. Alternatively, there is also the possibility of hybridization of the detectors or at least of one detector, wherein one detector has in part integrating, in part counting detector elements installed in it. Reference is made in FIGS. 2 to 4 to the exemplary layouts of the differently operating detector elements.

Both emitter-detector systems pass across a field of view located in the central circular opening. The patient 7 can be conveyed through this field of view along the system axis 9 with the aid of the patient couch 8. Basically, both a spiral scan and a sequential scan can hereby be performed. To improve the imaging of blood vessels or other structures a contrast agent can also be injected into the patient via a contrast agent applicator 11. Cardiac actions can in addition be scanned via the ECG line 12 in order to carry out cardiac action-triggered scanning and/or reconstruction.

Control of the CT system 1 and the evaluation of the scan of the patient 7 are carried out by the computer system 10 connected thereto, wherein this has at least one memory in which computer programs Prg1-Prgn are stored. According to the invention programs are contained or stored therein which are embodied such that during operation of the system they perform different embodiments of the inventive method.

Figure 2:
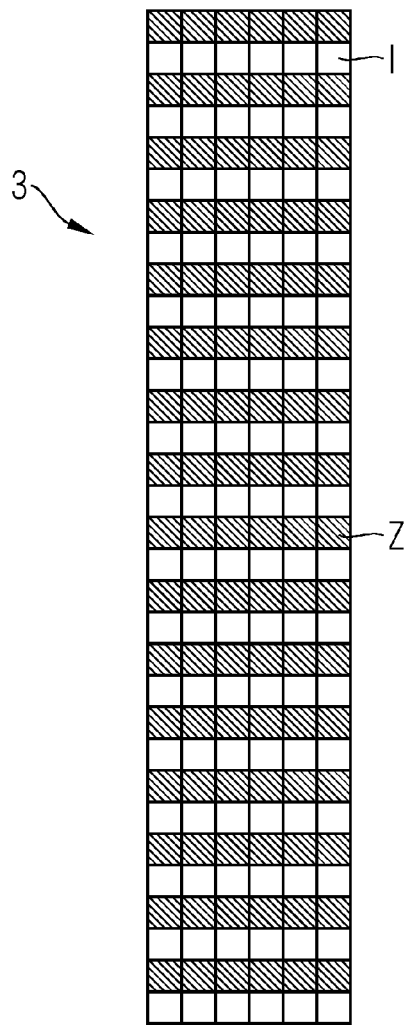
FIG. 2: View from above onto a detector with integrating detector elements on one side and counting detector elements on the other, grouped into rows.
Figure 3:
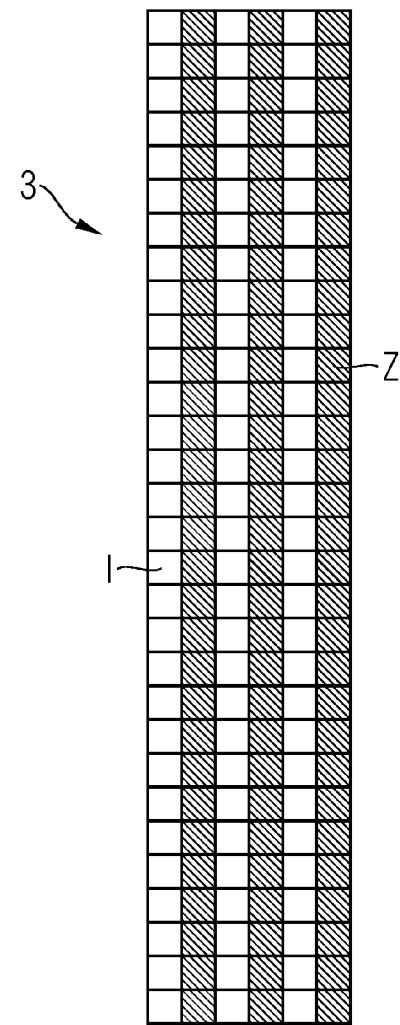
FIG. 3: View from above onto a detector with integrating detector elements on one side and counting detector elements on the other, grouped into lines.
Figure 4:
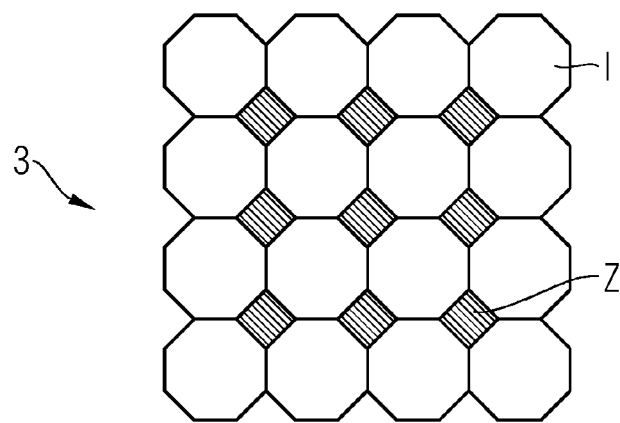
FIG. 4: View from above onto a detector with octagonal integrating detector elements arranged in a honeycomb pattern and counting detector elements in the gaps.

Examples of various mixed arrangements of integrating and counting detector elements in a, in some cases also the only, detector of a CT system are shown in FIGS. 2 to 4.

FIG. 2 depicts one embodiment of a hybrid detector with integrating (shown in non-hatched form), and counting (shown in hatched form) detector elements I, Z arranged alternately in rows. Such an arrangement is particularly suitable in the case of circular scans, as here upon rotation each integrating detector element I is followed by a counting detector element Z and it is very simple to find congruent rays through the scanned measurement object, which have been scanned by both types of detector elements, in order to compare these and where applicable to carry out the correction of the measurement data from the counting detector elements.

The layout shown in FIG. 3 is in particular advantageous for use in spiral scans. Integrating (shown in non-hatched form) and counting (shown in hatched form) detector elements I, Z are shown here arranged alternately in lines. As in the case of a spiral scan, an advancement in the direction of the system axis is performed, the same or at least almost the same rays traversing the measurement object again pass over both types of detector elements I, Z in order to allow comparison of the associated measurement results and where applicable to enable a correction to be made to the measurement data of the counting detector elements Z. If it proves impossible to find precisely overlapping rays from both sets of measurement data, the possibility exists by way of appropriate interpolation operations which are known per se to identify interpolated measurement data for congruent, if applicable also opposite rays.

It is pointed out here that it is also within the scope of the invention for the counting detectors, with reference to their projection surface, to use smaller detector elements Z than is the case with integrating detector elements. For example each surface of a counting detector element shown here can also be subdivided several times—for example into 2×2, 3×3 or 4×4 separately readable subsidiary surfaces, thus delivering significantly higher spatial resolution.

Another advantageous variant of a hybrid arrangement of counting and integrating detector elements Z, I is shown in FIG. 4. Here the integrating detector elements I (shown in non-hatched form) are produced in a honeycomb pattern from octagonal surfaces, wherein significantly smaller counting detector elements Z are inset into the rectangular spaces formed in the surface, which thus not only enable an energy resolution of the recorded spectrum, but also define finer measurement rays.

It can also be advantageous if when dispensing with a scatter radiation grid in front of the detector with the aid of the counting, that is energy-resolving detector elements Z, the current scatter radiation distribution in each position of the detector resulting from the scatter radiation spectrum differing from the original radiation spectrum is determined, and this scatter radiation value is in each case subtracted directly from the overall incoming radiation, including in the case of the integrating detector elements I.

Thus overall an embodiment of the invention describes a method and/or a computed tomography system for generating tomographic image datasets of a measurement object with multiple simultaneously operable sets of detector elements, wherein essentially at least one first set measures incident radiation over the entire energy spectrum of the incident radiation in an integrating manner and at least one second set measures incident radiation in at least two energy ranges in a resolving manner, wherein furthermore by way of the integrating measurements, the energy-resolving measurements relating in each case to rays traversing a measurement object in a spatially identical manner are corrected, and a tomographic image dataset of the measurement object is reconstructed at least from the corrected energy resolving measurements.

Although it has been illustrated and described in closer detail by way of the preferred example embodiment, the invention is not limited by the disclosed examples, and other variations can be derived therefrom by the person skilled in the art without leaving the scope of protection of the invention.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for generating tomographic image datasets of a measurement object with the aid of a computed tomography system with at least two simultaneously operable sets of detector elements to scan a measurement object from a multiplicity of projection angles, the method comprising:
    measuring, via at least one first set of integrating detector elements, incident radiation over an entire energy spectrum of the incident radiation in an integrating manner;
    measuring, via at least one second set of counting detector elements, incident radiation in at least two energy ranges in a resolving manner;
    correcting, by way of the integrating measurements of the at least one first set of integrating detector elements, the energy-resolving measurements of the at least one second set of counting detector elements relating to rays traversing a measurement object in a spatially identical manner; and
    reconstructing at least one tomographic image dataset of the measurement object at least from the corrected energy-resolving measurements of the second set of counting detector elements.

2. The method of claim 1, wherein a specific correction factor is formed for each counting detector element.

3. The method of claim 1, wherein measurement data of counting detector elements in the saturation range of the counting detector elements is replaced by direct or interpolated measurement data of the integrating detector elements.

4. The method of claim 2, wherein measurement data of counting detector elements in the saturation range of the counting detector elements is replaced by direct or interpolated measurement data of the integrating detector elements.

5. A computer readable medium including program segments for, when executed on a computer device, causing the computer device to implement the method of claim 1.

6. A computed tomography system, comprising:
- at least two simultaneously operable sets of detector elements for simultaneous scanning of an object under examination from a multiplicity of projection angles, at least one first set of integrating detector elements being designed for integrating radiation measurement and at least one second set of counting detector elements being designed to resolve an incident radiation spectrum into at least two energy bins; and
- a computer system for evaluation of measurement results of the detector elements with a memory including computer programs contained therein, at least one computer program, when executed, performing
  - measuring, via at least one first set of integrating detector elements, incident radiation over an entire energy spectrum of the incident radiation in an integrating manner;
  - measuring, via at least one second set of counting detector elements, incident radiation in at least two energy ranges in a resolving manner;
  - correcting, by way of the integrating measurements of the at least one first set of integrating detector elements, the energy-resolving measurements of the at least one second set of counting detector elements relating to rays traversing a measurement object in a spatially identical manner; and
  - reconstructing at least one tomographic image dataset of the measurement object at least from the corrected energy-resolving measurements of the second set of counting detector elements.

7. The computed tomography system of claim 6, wherein the at least one first set of integrating detector elements and the at least one second set of counting detector elements are each arranged on physically different detectors.

8. The computed tomography system of claim 6, comprising the at least one first set of integrating detector elements and the at least one second set of counting detector elements are arranged on one detector.

9. The computed tomography system of claim 8, comprising the integrating detector elements of the at least one first set and the counting detector elements of the at least one second set are arranged grouped into lines in the one detector.

10. The computed tomography system of claim 8, comprising the integrating detector elements of the at least one first set and the counting detector elements of the at least one second set are arranged grouped into rows in the one detector.

11. The computed tomography system of claim 8, comprising the integrating detector elements of the at least one first set and the counting detector elements of the at least one second set are arranged grouped in a checkerboard fashion in the one detector.

12. The computed tomography system of claim 6, wherein the populated surface of each of the counting detector elements is relatively smaller than the surface of each of the integrating detector elements.

13. The computed tomography system of claim 7, wherein the populated surface of each of the counting detector elements is relatively smaller than the surface of each of the integrating detector elements.

14. The computed tomography system of claim 8, wherein the populated surface of each of the counting detector elements is relatively smaller than the surface of each of the integrating detector elements.

15. The computed tomography system of claim 9, wherein the populated surface of each of the counting detector elements is relatively smaller than the surface of each of the integrating detector elements.

16. The computed tomography system of claim 10, wherein the populated surface of each of the counting detector elements is relatively smaller than the surface of each of the integrating detector elements.

17. The computed tomography system of claim 11, wherein the populated surface of each of the counting detector elements is relatively smaller than the surface of each of the integrating detector elements.

* * * * *